United States Patent [19]

Sherman

[11] Patent Number: 5,406,018
[45] Date of Patent: Apr. 11, 1995

[54] HOMOGENOUS CATALYST AND PROCESS FOR LIQUID PHASE ISOMERIZATION AND ALKYLATION

[75] Inventor: Larry G. Sherman, Edmond, Okla.

[73] Assignee: Kerr-McGee Corporation, Oklahoma City, Okla.

[21] Appl. No.: 993,601

[22] Filed: Dec. 21, 1992

[51] Int. Cl.⁶ .......................... C07C 2/60; C07C 5/27
[52] U.S. Cl. ................................ 585/729; 528/727; 528/728; 528/734; 528/741; 528/747
[58] Field of Search ............... 585/734, 741, 740, 746, 585/747; 582/721, 727, 729, 709, 742, 745

[56] References Cited

U.S. PATENT DOCUMENTS

| | | | |
|---|---|---|---|
| 3,470,264 | 9/1969 | Mayhue | 585/728 |
| 3,862,257 | 1/1975 | Buben et al. | 502/121 |
| 3,873,635 | 3/1975 | Prescott et al. | 585/717 |
| 3,880,945 | 4/1975 | Kramer et al. | 585/746 |
| 4,120,912 | 10/1978 | Hulme | 585/374 |

*Primary Examiner*—Anthony McFarlane
*Attorney, Agent, or Firm*—Herbert M. Hanegan

[57] ABSTRACT

A discrete catalyst and processes for the isomerization of alkanes and the alkylation of isoalkanes under homogenous fluid conditions. The catalyst is formed by contacting, under fluid conditions, a homogenous fluid containing a paraffin hydrocarbon having from 4 to 12 carbon atoms with a Lewis acid/protic Bronsted acid pair and a transition metal to produce a discrete catalytic complex that is soluble in the fluid. The discrete catalyst is the reaction product of the acid pair and alkanes and includes hydrocarbon ligands of limited chain length rendering it soluble in the fluid. The catalyst is active for the isomerization of alkanes and olefins, and the alkylation of isoalkanes, under homogenus fluid conditions.

35 Claims, 4 Drawing Sheets

HOMOGENOUS CATALYST AND PROCESS FOR LIQUID PHASE ISOMERIZATION AND ALKYLATION

BACKGROUND OF THE INVENTION

1. Field of the Invention

The invention provides a homogenous reaction medium and process for using a homogenous Lewis acid-hydrocarbon complex catalyst for producing an alkylate product that is blendable into motor gasolines. Further, the invention provides a method for using a homogenous catalyst for converting normal alkanes to isoalkanes. Isoalkanes and olefins may then be further subjected to an alkylation reaction to form alkylates suitable for blending into motor gasolines.

2. Description of the Related Art

Typical unleaded motor gasolines sold in various octane grades in the United States today are produced by blending together various component streams that are the end products of a variety of hydrocarbon refining processes. For example, a typical gasoline blend may contain, as its components, hydrocracker gasoline produced by catalytic hydrogenation in a "hydrocracking" unit, cracked gasolines produced by a fluidized catalytic cracker, reformate produced by the catalytic reformation of naphtha, isopentane produced by the catalytic isomerization of normal pentane, alkylate produced by the acid alkylation of isobutanes and olefins, normal butane produced from the distillation of crude oil or natural gas, etc. In order to produce gasolines having a specific octane rating and other specific properties, such as vapor pressure, the relative amounts of these component streams in the gasoline blend are adjusted. For example, if it is desired to produce a higher octane rated gasoline, then a larger proportion of the higher octane rated components will be added while lower octane components will be reduced or removed from the blend.

By way of background regarding octane ratings, it has long been recognized that highly branched hydrocarbons and aromatic hydrocarbons, such as benzene, toluene and xylene, have high octane numbers. This means that when these hydrocarbons are mixed with air under temperature and pressure conditions sufficient to permit complete vaporization, and the mixture is ignited, they burn with a steady rate of combustion and do not burn explosively. Explosive combustion or "knocking" will cause damage to internal combustion engines, if continued for any prolonged period of time. The oil refining industry has developed standards and methods for comparing the combustion of various hydrocarbons and blends of hydrocarbons. 2,2,4 trimethylpentane (commonly called "isooctane") is arbitrarily assigned an octane value of 100 and all other gasoline blending components are compared with this standard.

Alkylates are produced by an acid catalyzed reaction of an alkene with an isoalkane. The alkylate product stream comprises a mixture of multiply branched hydrocarbon compounds of increased carbon number. Highly branched hydrocarbon compounds, such as the trimethyl pentanes, are greatly valued as components for gasoline blends in order to increase the "octane" rating of the gasoline or otherwise modifying other properties of a gasoline fuel.

During the 1930's aircraft of increasing performance required the production of aviation fuels of increased performance, one important property of which was that of a higher octane rating. The highly branched hydrocarbon compounds of a high "octane" rating—such as 2,2,4 trimethylpentane, commonly known as "isooctane," and assigned a 100 octane rating—were not naturally abundant enough in crude oil to be produced in the quantities required for blending with gasoline to meet the quantity demands for high octane aviation fuel.

This gave rise to an intensive study during this early period of methods for producing highly branched alkanes in the gasoline fraction boiling range having high octane properties by reacting lower olefins with lower isoalkanes. There was little economic value in the 1930's-1940's for ethylene or lower isoalkanes, such as isobutane, which further provided incentive to the effort to convert them to highly valuable hydrocarbon products, such as high octane value blending compounds for gasoline fuels.

One method for preparing high octane value hydrocarbons which was developed during this period comprised exposing ethylene and isobutane to an acid-pair composition comprising a metal halide-type Lewis acid and a protic Bronsted acid—most commonly the Lewis acid being $AlCl_3$ and the protic Bronsted acid being HCl. Under such conditions the ethylene and isobutane react in the presence of the acid pair composition to form multiply branched hydrocarbon compounds of a $C_6$-$C_8$, and higher, carbon number, known as an "alkylate" product.

There are many reports in the literature of the 1930-1960 period on "alkylation" with a Lewis acid-Bronsted acid type of catalyst. See for example R. C. Alden et al., "Diisopropyl", *The Oil and Gas Journal*, pp. 70-73, 103-107 (Feb. 9, 1946); Clark Holloway et al., "Pilot Plant Production of 2,3-Dimethylbutane", *Industrial and Engineering Chemistry*, Vol. 38, No. 12, pp. 1231-1238 (Dec. 1946); R. B. Thompson et al., "Production of 2,3-Dimethylbutane by Alkylation", Vol. 40, No. 7, pp. 1265-1269 (July 1948); R. S. Manne, U.S. Pat. No. 2,674,637 (1954); and L. F. Mayhue, U.S. Pat. No. 3,470,264 (1969); and G. F. Prescott et al. U.S. Pat. No. 3,873,635 (1975). As was typical in all such processes, the acid-pair catalyst composition, an aluminum chloride-hydrocarbon complex, formed as a "red oil" or sludge which was not miscible in the ethylene-isoalkane-alkylate hydrocarbon liquid phase. Typically the volume ratio of hydrocarbon feed to red oil catalyst volume ranged from about 1:1 to 1:3 and the reaction had to be performed under vigorous agitation conditions. Further, the activity of the acid-pair catalyst composition eroded over time and as the content of red oil or acid sludge increased. This made it necessary to continuously supply fresh makeup catalyst to the reaction zone while removing then disposing of spent catalyst sludge.

As time progressed, certain events occurred which displaced the acid pair method of alkylate production from commercial use. Non-alkylate octane booster additives were devised—such as the tetraethyl lead of "leaded" gasoline—and other methods were devised for production of alkylate streams, such as by HF and/or $H_2SO_4$ acid alkylation. Further, as the polymer industry began to develop and polyethylene came into great demand, ethylene achieved a high product value as a monomer and it became economically undesirable to utilize ethylene for alkylate production.

More recently, with the discovery of the health hazards associated with lead, tetraethyl lead has fallen into disrepute as an octane booster and production of "leaded" gasolines has been banned. This lead to the utilization of aromatic hydrocarbons as octane boosting gasoline additives—such as a combination of benzene-toluene-xylene—for the production of premium unleaded gasoline.

Commercial alkylation plants today may be divided into two categories, those that use sulfuric acid as the catalyst and others that use hydrogen fluoride (HF) as the catalyst for the alkylation reaction. While the sulfuric acid process is the older of the two, the relative importance of the hydrogen fluoride process has increased substantially in recent years so the HF-plants now produce about 47% of all alkylate. By the end of 1990 it was estimated that about 11% of the total gasoline pool consisted of alkylates produced by alkylating isobutane with $C_3$–$C_5$ olefins. Further, alkylation capacity in the United States totaled about 960,000 b/d of alkylate.

Both HF and sulfuric acid alkylation processes are postulated to proceed by the same overall reaction:

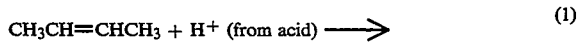  (1)

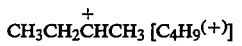

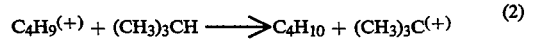  (2)

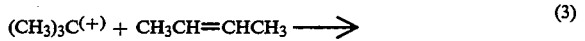  (3)

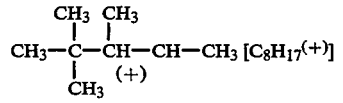

  (4)

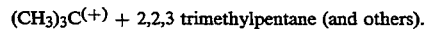

Thus, a postulated isobutyl cation reacts with an olefin (here 2-butene) to form a branched $C_8$ cation which in turn reacts with another isobutane molecule to form a neutral $C_8$ hydrocarbon (2,2,3 trimethylpentane) while regenerating another isobutyl cation. However, a number of competing side reactions also occur, the most troublesome of which produces polymerized olefins ("conjunct polymers" or "tars") which are more soluble in the acid phase than in the isobutane phase. The acid catalyst is not miscible with the hydrocarbon phase (isobutane/2-butene/alkylate hydrocarbon) and the reaction is accomplished under vigorous agitation. The undesired polymerization reaction proceeds in the acid phase. In contrast, the desired alkylation reaction takes place predominantly at the acid/oil interface. To minimize formation of these polymers or tars and maximize alkylate yield, several operating variables are controlled: the acid:oil ratio in the reactor is minimized; the acid/oil interface is increased by high turbulence; olefin is diluted by a high isobutane:olefin ratio; and reactor temperature is maintained as low as possible.

During the alkylation of isobutane with $C_3$–$C_5$ olefins a portion of the acid catalyst is consumed. For instance, in sulfuric acid catalyzed alkylation, about 0.4–0.6 pounds of sulfuric acid is frequently required to produce about 1 gallon of alkylate, but much lower values, such as 0.1–0.25 pounds per gallon (ppg), can be realized at preferred conditions. Acid costs frequently account for about one third of the total operating costs of sulfuric acid catalyzed alkylation units.

In hydrogen fluoride catalyzed alkylation, HF consumption is often in the range of 0.08–0.25 ppg and regeneration of used HF is relatively easy and cheap. Further, since most of the HF is recovered and recycled, the amount of makeup HF required is small, usually about 0.15–0.2 pounds/bbl of alkylate. However, the conjunct polymers produced with HF alkylation may contain some residual HF and therefore pose a problem of environmentally acceptable disposal.

It now appears that the aromatic hydrocarbon octane boosters produce health hazards, such as being possibly carcinogens, as well as being contributors to ozone formation. The phaseout of aromatics as octane boosters will greatly increase the demand for high octane value alkylates, with their present day method for production giving rise to other concerns.

Aside from the problem of safely disposing of conjunct polymers produced in HF alkylation units, there is also growing public concern about the safety of HF alkylation units. When HF is released into the atmosphere, it forms a fine aerosol which appears to remain at ground level and is then transported by wind. In the event of a release of HF into the air, a concentration in the range of about 2–10 ppm causes irritation of the eyes, skin and nasal passages. Concentrations of about 20 ppm result in immediate danger to life and health. As a result of the hazards posed by inadvertent release of HF from HF alkylation plants, there is a need to develop other technologies for producing alkylate that do not have these attendant risks.

In A. K. Roebuck et al, "Isobutane-Olefin Alkylation With Inhibited Aluminum Chloride Catalyst," *Ind. Eng. Chem, Prod. Res. Develop.*, Vol. 9. No. 1 (March 1970) a renewed focus was given to an aluminum chloride type of catalyst which would dissolve more isobutane, to minimize production of heavy end products compared to HF or $H_2SO_4$ alkylation procedures, while also minimizing non-favored by-product as is typical with $AlCl_3$ based catalyst. An aluminum chloride-ether complex catalyst is described, which in conjunction with various inhibitors, appears capable of giving the desired results under certain conditions. Again, as typical with an aluminum chloride type catalyst, the catalyst phase is not miscible with the hydrocarbon phase, and the reaction medium is a non-homogeneous emulsion produced by vigorous agitation.

There exists a need for a high octane gasoline blending component which is not hazardous to health or the environment to replace aromatic components in the gasoline pool. While this need may be fulfilled by alkylate blending components, there yet exists a need for an alkylation process that is free of the perceived risks to human health and life associated with the use of the HF alkylation process, the tar disposal problem posed by both the sulfuric acid and the HF alkylation processes and the red oil problems associated with the use of an $AlCl_3$ type catalyst. Further, it is desirable to develop a process of alkylation that utilizes less catalyst in the reactors and held in inventory.

SUMMARY OF THE INVENTION

The invention provides for the formation of a homogeneous reaction medium containing a dissolved catalyst and a process for the isomerization of alkanes and the alkylation of alkanes with olefins within the homogeneous reaction medium. The alkanes to be isomerized desirably have from about 4 to about 12 carbon atoms. Similarly, the isoalkanes to be alkylated also have from about 4 to about 12 carbon atoms.

The process utilizing this homogeneous medium is carried out at fluid conditions wherein the catalyst is dissolved in a fluid containing a paraffin hydrocarbon. As a result of the homogenous phase created, the isomerization and alkylation reactions proceed rapidly at temperatures of at least about 140° F. (60° C.) with high selectivity and at high conversion in the presence of a Lewis acid catalyst complex which is in solution in the medium in amounts which provide a concentration of Lewis acid of from about $7.5 \times 10^{-3}$ to about $15.0 \times 10^{-3}$ millimoles of dissolved Lewis acid per gram of medium. With respect to a preferred Lewis acid, an aluminum chloride, the catalyst complex is in solution in amounts from about 200 to about 410 ppm of aluminum. The process minimizes the production of conjunct polymers and undesirable or toxic waste products that pose problems with respect to environmentally safe disposal. Further, the process of this invention generally does not utilize hydrofluoric acid, in the manner and quantity in which it is used in the hydrofluoric alkylation processes, thereby eliminating the potential risk to human health by eliminating the risk of the formation of a hydrofluoric acid aerosol in the event of an unintended partial loss of the reactor contents.

The catalyst composition comprises a metal halide-type Lewis acid and a protic Bronsted acid as an integral part of the Lewis acid-hydrocarbon complex catalyst. It is desirable that the protic acid have an anion corresponding to the anionic component of the Lewis acid. The Lewis acid-hydrocarbon complex catalyst composition may further comprise a transition metal cation obtained from a metal selected from Groups 1b, 6b, 7b, and 8 of the Periodic Table, that is able to undergo redox reactions. The acid pair is associated to at least one hydrocarbon "chain" or "ligand" which is a hydrocarbyl radical having a formula $C_nH_{2n+1}$ wherein n is at most about 12, or which is an ether. The Lewis acid most preferred for formation of the catalyst is a di or trichloride of aluminum.

The invention comprises the formation of a homogenous reaction medium containing a Lewis acid-hydrocarbon complex catalyst dissolved in a fluid containing a paraffin hydrocarbon and uses of the homogeneous reaction medium containing the dissolved catalyst to (1) isomerize normal alkanes under homogenous fluid conditions to isoalkanes; or (2) to catalyze the reaction of isoalkanes with olefins under homogeneous fluid conditions to produce an alkylate product stream. The homogeneous reaction medium containing dissolved catalyst can be produced as a liquid phase solution or a supercritical fluid solution and employed in such fluid state to catalyze the desired reaction—isomerization or alkylation—under homogeneous liquid phase or supercritical fluid phase conditions. For supercritical fluid phase operation, the desired reaction can be, and preferably is, accomplished in a continuous plug flow manner in a reaction vessel designed to minimize turbulence within the reaction medium.

Upon completion of the desired reaction the separation of catalyst from the hydrocarbon content of the fluid medium may be readily accomplished. If reaction is performed under supercritical fluid conditions, catalyst separation by precipitation is readily accomplished by slight increases of temperature or reductions of pressure on the reaction medium; whereas if reaction is performed under liquid phase conditions the hydrocarbon content of the medium may be separated from the catalyst by flashing or alternatively by subjecting the liquid medium to an absorbent for the catalyst. The recovered catalyst may be recycled for reuse with feeds of fresh makeup reagents to form fresh charges of a homogenous reaction medium for further reaction.

The catalyst composition comprises a hydrocarbon soluble complex which forms upon the interaction of a metal halide-type Lewis acid and a protic Bronsted acid with a paraffin or ether hydrocarbon.

The nature of the hydrocarbon for the homogeneous reaction medium will depend upon the type of reaction desired to be accomplished within the medium. For the isomerization of a normal alkane to an isoalkane product the normal alkane reactant itself may be used as the fluid component of the medium. Wherein alkylation is to be accomplished, the isoalkane reactant may be used as the fluid component of the medium. When the desired reaction—isomerization or alkylation—is to be carried out under liquid phase condition the hydrocarbon reactant(s) can be used as the sole fluid component(s) for the medium. Wherein the reaction is to be carried out under supercritical fluid conditions, in addition to the hydrocarbon reactant, a solvent may be used to achieve a fluid mixture of a critical temperature which is lower than that of the alkane reactant alone. The "solvent" which may be used as a component in the supercritical fluid mixture, may be any polar or nonpolar, inert solvent known to have a critical temperature between about $-110°$ and $400°$ F. ($-79°$ to $204°$ C.). These solvents include methane, ethane, propane, sulfur dioxide, carbon dioxide, nitrogen oxides (e.g., $N_2O_3$, NO, $NO_2$), the low molecular weight fluorocarbons, or halocarbons, the rare gas elements (argon or xenon), and the like.

Production of the homogeneous reaction medium containing dissolved catalyst can be accomplished in a variety of ways. The fluid component of the medium can be brought into contact with a source of solid Lewis acid simultaneously with contacting it with a Bronsted acid, then the fluid removed from further contact with the solid Lewis acid to produce a homogeneous fluid solution of the two components. More preferably, the fluid component of the medium is brought into then removed from contact with the solid Lewis acid before the Bronsted acid component is added to the fluid. Alternatively a soluble catalyst can be produced by reacting the dissolved Lewis acid with an alkyl halide which at the temperature for isomerization or alkylation reaction decomposes into an alkene and a hydrogen halide acid.

DETAILED DESCRIPTION OF THE PREFERRED EMBODIMENTS

Figure 1:
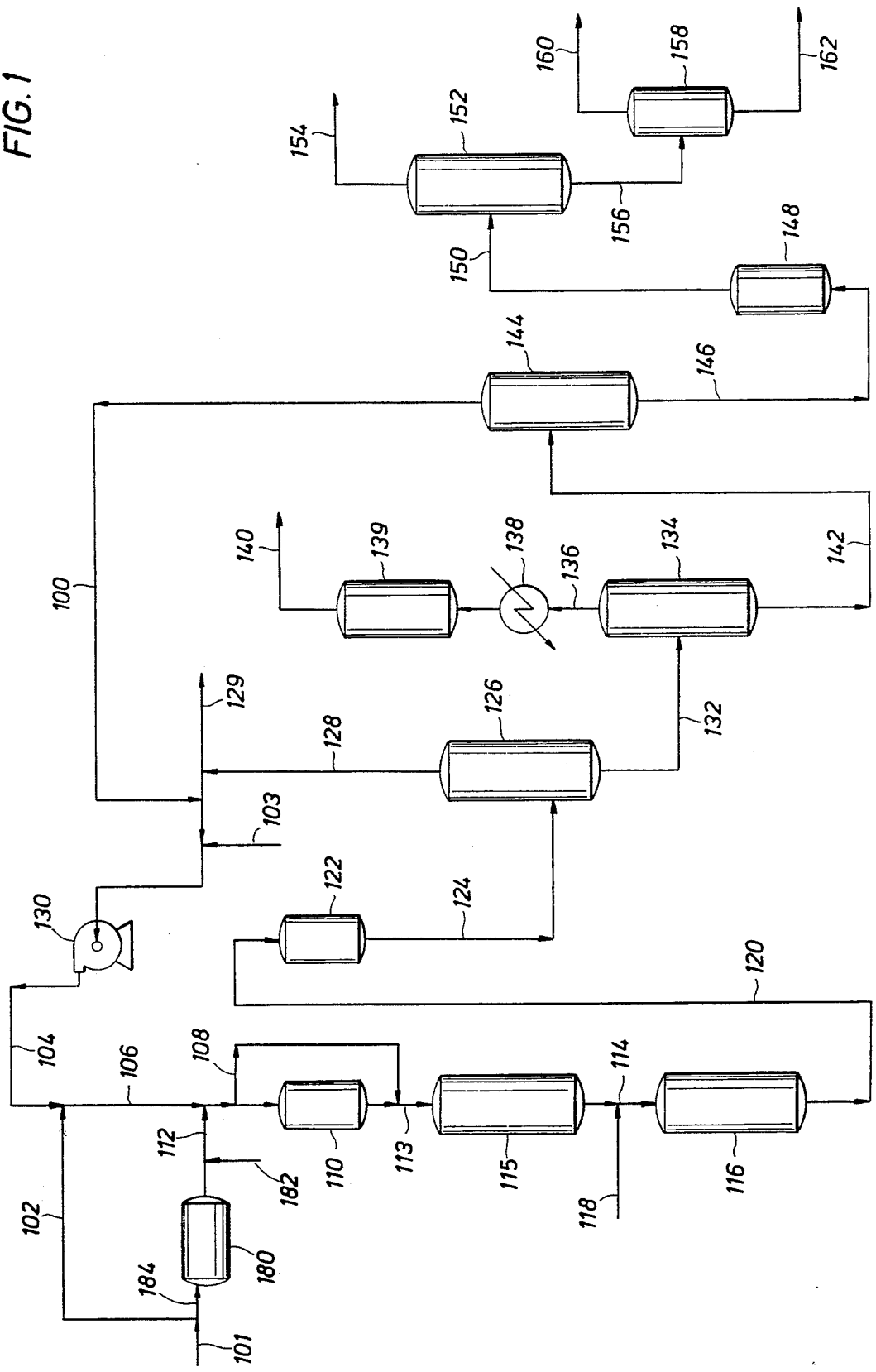
FIG. 1 is a simplified flow diagram of an embodiment of the invention illustrating the invention isomerization and alkylation processes as practiced under supercritical fluid phase conditions.

The invention provides a catalyst, a method for producing this catalyst, and processes for utilizing the catalyst in isomerization and alkylation reactions conducted in a homogeneous reaction medium. The isomerization process is applicable to alkane feedstocks wherein the alkane comprises from 4 to 12 carbon atoms. The alkylation process combines isoalkanes having from 4 to 12 carbon atoms with olefins having from 2 to 9 carbon atoms.

For isomerization reactions, this invention is particularly applicable to normal alkanes comprising from about 4 to about 12 carbon atoms. The normal alkanes having from 4 to about 8 carbon atoms are preferred charge stocks, and those having from 4 to 6 carbon atoms are more preferred since these hydrocarbons isomerize to isoalkanes which are typically used to produce alkylate products for gasoline blends. The most preferred normal alkane is n-butane which isomerizes to iso-butane.

The alkane serves a plurality of functions in the process of this invention. It is a reactant which undergoes the desired isomerization or alkylation reactions, in the presence of the dissolved Lewis acid-hydrocarbon complex catalyst. However, a portion of the alkane also serves as a reagent in the formation of the dissolved catalyst complex which catalyzes the desired isomerization and alkylation reactions. Further, the alkane also serves as a component of the fluid in which the catalyst complex is soluble. Thus, the alkane forms a part of the homogenous fluid medium wherein the reaction occurs by which the hydrocarbon reactant is reacted to produce a product hydrocarbon of a different molecular structure.

The Fluid of the Reaction Medium

In accordance with this invention, the desired reaction—isomerization or alkylation—is carried out within a homogenous fluid medium. The fluid of the reaction medium may be a liquid hydrocarbon or a supercritical fluid containing a paraffin.

Liquid Phase Fluids

When liquid phase reaction conditions are selected for the practice of this process, the fluid for the reaction medium is preferably a liquified hydrocarbon which is also a reactant hydrocarbon in the process. For an isomerization reaction, the fluid would preferably be an n-alkane, particularly n-butane being preferred since these hydrocarbons in addition to serving as the fluid of the reaction medium undergo an isomerization reaction therein to produce isobutane. For an alkylation reaction, the fluid of the reaction medium is preferably selected to be the isoalkane which is a reactant for the olefin reactant of the alkylation process. Again, in this case the isoalkane serves the function of a fluid for forming the homogenous reaction medium and also as a hydrocarbon reactant in that medium. In a preferred embodiment of a liquid phase alkylation reaction according to the invention, the fluid of the reaction medium is iso-butane.

In the case of a liquid phase reaction, the hydrocarbon selected as the fluid for the reaction medium will be maintained at a temperature below its critical temperature and under a pressure sufficient to maintain the hydrocarbon in the liquid state while forming the Lewis acid-hydrocarbon complex catalyst and during conduction of the selected isomerization or alkylation reactions.

For the isomerization of a n-alkane, such as n-butane, n-pentane or n-hexane, to its corresponding iso-alkane product, that n-alkane would be selected as the fluid in which to form the dissolved Lewis acid-hydrocarbon complex to yield the homogenous medium for the reaction. Accordingly, when forming the catalyst or conducting the isomerization reaction the temperature of the n-alkane fluid may not exceed the critical temperature of that n-alkane or the i-alkane/n-alkane product mixture, whichever is lower. For isomerization, n-butane is preferred as the fluid, isobutane is produced as the product, and the temperature of the fluid should not exceed 305° F. (152° C.).

For an alkylation reaction, the isoalkane which participates in the reaction is selected as the fluid for the homogeneous reaction medium. During the alkylation reaction the isoalkane should normally be present in the medium in a molar ratio to the olefin reactant of at least about 5:1 and greater. Accordingly, for liquid phase reaction the temperature of the isoalkane fluid should not exceed the critical temperature of the selected isoalkane. For alkylation isobutane is preferred, and the temperature of the fluid should not exceed 275° F. (135° C.).

Generally an alkylation reaction can be accomplished at a lower temperature than a paraffin isomerization reaction. For alkylation, the homogeneous reaction medium should be maintained at a temperature of at least about 140° F. (60° C.), whereas for isomerization a temperature of at least about 200° F. (93° C.) is preferred. For liquid phase alkylation wherein the catalyst is composed of an aluminum chloride, the fluid temperature should be maintained at a temperature of from about 140° to 220° F. (60° to 105° C.), more preferably from about 180° to 220° F. (82° to 105° C.), and most preferably from about 190° to 220° F. (88° to 105° C.).

Supercritical Fluids

The homogenous reaction medium may, as an alternative embodiment, be formed as a supercritical fluid. A supercritical fluid is not a liquid, nor does it exhibit the properties of a gas; instead it exhibits solubility properties more like that of a liquid than a gas, and molecular diffusion properties more like that of a gas than a liquid; hence is referred to in the art as a "super-critical fluid."

For purposes of this invention the supercritical fluid may be comprised of components which, under normal conditions of temperature and pressure would be normally liquid components or a mixture of normally liquid and normally gaseous components. In the first situation wherein the component of the supercritical fluid is a normally liquid component this component is elevated in temperature above its critical temperature and maintained under a pressure sufficient to produce a fluid phase of a density at least 0.1 times that of the pure component when saturated in its liquid state at 68° F. (20° C.). In the second situation, the components being a mixture of a normal liquid and a normal gas, the gas component functions as a "solvent" for the liquid such that the mixture has a lower critical temperature than does the liquid component alone. As a consequence the liquid-gas mixture can be formed into a supercritical fluid at lower temperatures than could the liquid component alone.

One specific situation wherein it is preferred to utilize a solvent is in the isomerization of n-butane to isobutane. In the absence of a solvent a temperature exceeding 300° F. is needed to transform n-butane from a liquid phase to a supercritical fluid. With the use of a solvent such as propane, a mixture is produced which can be rendered into a supercritical fluid at temperatures of 200° F. or less. The equilibrium for conversion of n-butane to iso-butane is more favorable at lower temperatures.

The "solvent" or "co-solvent" which may become a component in the supercritical fluid mixture, may be any polar or non-polar, inert solvent known to have a critical temperature between about −110° and 400° F. (−79° and 204° C.). These solvents include methane, ethane, propane, sulfur dioxide, carbon dioxide, nitrogen oxides (e.g. $N_2O_3$, NO, $NO_2$), the low molecular weight fluorocarbons, or halocarbons, the rare gas elements (argon or xenon), and the like. By inert, it is meant that the solvent does not reactively interfere in the formation of the catalyst, the isomerization or alkylation reactions to produce a separate product. The preferred solvents include ethane and carbon dioxide, and the most preferred solvent is ethane.

In the context of this invention, the solvent primarily serves as the component of the supercritical mixture which provides the mixture with the pressure and temperature properties most preferred for the reaction in the supercritical state. This supercritical state allows both the formation and the solubilization of the Lewis acid-hydrocarbon complex catalyst.

"Supercritical conditions" refer to conditions where the temperatures are above the critical temperature of the solvent-hydrocarbon mixture and a pressure sufficient to impart a density to the mixture which is at least equal to 0.1 of the density of the pure solvent when saturated in its liquid state, at 68° F. Preferably, the density of the mixture should be greater than about 0.25 times the density of the pure solvent saturated in its liquid state at 68° F. (20° C.). In general, a supercritical pressure will be in the range of about 600 to about 5,000 psia; preferably from about 700 to about 2,500 psia.

Choice of Fluid Type

The choice of the fluid as a liquid phase or as a supercritical fluid results in different operating economics. Generally, in a supercritical fluid medium the isomerization and/or alkylation reactions proceed at a higher rate than in liquid phase fluids. Following the reaction, catalyst complex can readily be separated from the hydrocarbon components of a supercritical fluid by changing the density of the supercritical fluid. Decreasing the density precipitates the catalyst from solution. The density may be decreased either by increasing the temperature or by lowering the pressure of the supercritical fluid, or by a combination of both. This involves a need for reheating and/or recompression of the unreacted excess isoalkane and solvent for recycle use, the cost of which may lead one to prefer a liquid phase reaction procedure. In a liquid phase procedure, the reaction medium following reaction may be allowed to undergo flash evaporation to separate the hydrocarbon components from the catalyst complex. Again the unreacted excess isoalkane would be recovered and recompressed—but to a lesser degree than required for supercritical operations—at a reduced recompression cost. Alternatively the liquid medium containing unreacted alkane, and heavier alkylate product and catalyst, may be routed over a bed of absorbent for the catalyst to separate it from the alkylate product.

The Catalyst

The invention provides a homogeneous catalyst for the isomerization and alkylation of olefins and alkanes. The catalyst comprises a Lewis acid of the metal halide-type, a protic Bronsted acid, and a hydrocarbon component. The Lewis acid-hydrocarbon complex catalyst is the product of reaction of at least (a) a Lewis acid of the formula $R_{m-2-z}MX_{2+x}$ wherein M is a Group 3a, 5a or 5b metal, X is a halide, R is a hydrocarbyl radical having 1 to 12 carbon atoms, "m" is an integer equal to the greatest oxidation state of M, and "z" is an integer of 0, 1 or m−2; (b) a hydrogen halide; and (c) an organic compound selected from (1) paraffins having 12 or fewer carbon atoms, (2) olefins having 12 or fewer carbon atoms, or (3) ethers having 6 or fewer total carbon atoms. All group references are with respect to the Periodic Table of Elements as published in *CRC Handbook of Chemistry and Physics*, 51st Edition (1970-71) published by The Chemical Rubber Co.

The useful Lewis acids include, for example, aluminum trihalides, alkylaluminum dihalides, aluminum oxychlorides, gallium trihalides, alkylgallium dihalides, boron trihalides, antimony pentahalides, tantalum pentahalides, and niobium pentahalides and the like. Of these, the fluorides of antimony, tantalum, niobium and boron are preferred while for aluminum and gallinium the chlorides are preferred. Most preferred as the Lewis acid component for the catalysts are chlorides of aluminum, such as aluminum trichloride, an alkylaluminum monochloride or alkylaluminum dichloride wherein the alkyl group has from 1 to 12 carbon atoms. Particularly preferred Lewis acids are aluminum trichloride and isobutylaluminum dichloride.

The Bronsted acids include the protic Bronsted acids that have an anion corresponding to the anion of the Lewis acid used. Thus, the Bronsted acid may be selected from hydrogen fluoride, hydrogen chloride, hydrogen bromide and hydrogen iodide. The preferred Bronsted acids are HCl and HBr. Since the most preferred Lewis acid is an aluminum chloride, the most preferred Bronsted acid is hydrogen chloride. The Bronsted acid may be supplied in the form of a Bronsted acid donor, namely a compound which at the temperature conditions for isomerization and/or alkylation reactions decomposes to yield a Bronsted acid. Such Bronsted acid donors are alkyl chlorides like butyl chloride, which decomposes into butene and hydrogen chloride.

The organic compounds which may be utilized in forming the catalyst are the alkanes and/or olefins which are to be utilized as the reagents for the isomerization or alkylation reaction. For an isomerization reaction the preferred organic compounds are normal butane, normal pentane, and normal hexane, with normal butane being most preferred. Alternatively, when forming the catalyst, the organic compound may be an ether such as dimethyl, diethyl or methylethyl ethers or combinations thereof. In this event the catalyst is best prepared by adding the ether to a stirred suspension of aluminum trichloride in a hydrocarbon solvent. Following the reaction of the aluminum trichloride and ether the resulting aluminum chloride-ether complex may be then be dissolved in a fluid containing a hydrocarbon and a Bronsted acid or Bronsted acid donor is added to such fluid to complete the formation of the catalyst complex.

The homogeneous medium containing the dissolved Lewis acid-hydrocarbon complex catalyst can be formed in a variety of ways. The fluid containing a hydrocarbon may be flowed through a bed of a solid Lewis acid, such as AlCl₃ to cause Lewis acid to dissolve in the fluid, then removed from further contact with the solid Lewis acid. Thereafter, a Bronsted acid or a Bronsted acid donor may be added to the fluid containing the dissolved Lewis acid. Wherein a Bronsted acid is added, the catalyst forms upon addition of the Bronsted acid. When a Bronsted acid donor, such as butyl chloride, is added, the catalyst complex forms when the fluid reaches a temperature at which the alkyl chloride ionizes in the presence of a Lewis acid.

It is preferred to solubilize the Lewis acid before adding the Bronsted acid or Bronsted acid donor. The preferred ratio of Bronsted acid or Bronsted acid donor to the Lewis acid halide is between 0.6 and 1.5 on a molar basis.

If desired, the activity of the Lewis acid-hydrocarbon complex catalyst may be modified by forming it in the presence of a transition metal halide wherein the transition metal is selected from Group 1b, 6b, 8b and 8 of the Periodic Table of Elements and is a metal which is able to undergo redox reactions. Silver chloride, copper chloride and iron chloride are examples of preferred transition metal halides which are useful for modifying the activity of the catalyst. When a transition metal halide modifier is employed, it is preferred to add it to the solubilized Lewis acid in an amount which provides for a molar ratio of transition metal halide to the dissolved Lewis acid of from about 0.5 to about 1.0.

The catalyst when formed as a Lewis acid-hydrocarbon complex may be represented by the following formula:

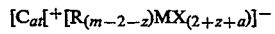

$$[Cat^+[R_{(m-2-z)}MX_{(2+z+a)}]]^-$$

wherein "Cat" is a carbocation, R is a hydrocarbyl radical having from 3 to 12 carbon atoms, M is a group 3a, 5a, or 5b metal or metalloid, X is halide, "m" is an integer equal to the greatest oxidation state of M, "z" is 0, 1, or m−2, and "a" is a number greater than 0.5 and less than 1.5. Accordingly, when forming this catalyst the Bronsted acid halide (HX) should be added to the dissolved Lewis acid ($R_{m-2-z}MX_{2+z}$) in an amount that provides a molar ratio of Bronsted acid halide to Lewis acid of 1:2 to 3:2. The catalyst when formed as a Lewis acid-ether complex may be represented by the following formula:

$$R'_2OM'X_3.sM'X_3.rHX$$

wherein each R' is an alkyl radical of from 1 to 3 carbon atoms and each R' radicals may be the same or different, M' is a trivalent Group 3a, 5a or 5b metal or metalloid, X is halide, "s" and "r" are greater than 0.05 and less than 0.1.

Formation of the Homogeneous Reaction Medium

The nature of the fluid phase as a liquid phase or as a supercritical fluid requires different methods for forming the homogeneous reaction medium. When liquid phase operation is selected the catalyst can be formed therein in a greater variety of ways than when a supercritical fluid operation is selected. The content of catalyst dissolved in the medium, expressed as a Lewis acid content, may range from about 3.0 to about 30 millimoles of Lewis acid/1000 g of medium, preferably from about 3.0 to 22.5 millimoles/1000 g of medium, and more preferably about 15 millimoles/1000 g of medium.

Supercritical Fluid Operation

The Bronsted acid may be selected from hydrogen fluoride, hydrogen chloride, hydrogen bromide, and hydrogen iodide. The preferred Bronsted acids are HCl and HBr. Since the most preferred Lewis acid is AlCl₃, the most preferred Bronsted acid is HCl. The Bronsted acid is an integral part of the discrete catalyst species so that at least some of it should be present to produce the active catalyst species in useful quantities. The discrete catalyst is desirably produced in such a concentration that it remains soluble in the alkane or alkane-solvent supercritical fluid. Thus, the catalyst may, when calculated as AlCl₃, be produced in the range from about 400 to about 4,000 ppm, preferably about 1,000 to about 3,000, most preferably about 2,000 ppm, based on the fluid weight. Desirably, the Bronsted acid should be present in a molar ratio with respect to the Lewis acid ranging from 0.5 to 1.5 preferably about 0.9 to 1.5, and most preferably 1.0 to 1.5.

As explained above, the useful alkanes are those comprising from 4 to 12 carbon atoms, preferably from 4 to 8 carbon atoms, and more preferably, from 4 to 6 carbon atoms. In its supercritical fluid state the alkane is desirably present in a solvent in a alkane:solvent molar ratio of from about 1:99 to about 50:50; preferably 10:90 to about 40:60 and most preferably 20:80 to 40:60.

To produce the invention catalyst, the Lewis acid, transition metal if desired, Bronsted acid, solvent and alkane are combined at supercritical conditions and within the above ranges of concentration in a catalyst formation reactor. Thus, the catalyst may be produced by contacting the preferred Lewis acid, AlCl₃, the preferred transition metal (either iron or copper), a supercritical fluid comprising an alkane, preferably normal butane, in the ratio from about 20:80 to about 30:70 with respect to a solvent, preferably ethane or propane, most preferably propane, and a Bronsted acid, preferably HCl, at about 1000 psia and 200° F. (93° C.). The Bronsted acid is preferably$^I$ added after the stream contains the Lewis acid.

If a Bronsted acid is present during the contact of an alkane with a solid Lewis acid, the contact time with the solid Lewis acid should be limited to a time sufficient to produce the discrete catalytic composition. Thus, in the preferred continuous process of forming the catalyst, a mixture of the alkane and solvent, would desirably flow over a surface that presents the Lewis acid and transition metal to the flowing supercritical fluid mixture in a catalyst formation reactor. The mixture's flow rate may then be adjusted such that the fluid is not in contact with the Lewis acid for more than about 10 minutes, preferably less than about 5 minutes, and most preferably less than about 3 minutes. The optimum residence time range will depend upon the specific Lewis and Bronsted acids, the alkane, and the temperature and pressure conditions. The Bronsted acid is then added.

It should be noted that for as long as the supercritical mixture of alkane, Bronsted acid, and co-solvent is in contact with a solid Lewis acid of the metal halide-type, oligomerization of the hydrocarbon chains of the catalyst will continue. By taking the supercritical fluid out of contact with the solid Lewis acid, the desired catalyst composition may be obtained as a discrete catalyst that is active for the isomerization of alkanes or olefins and also is active and selective for the alkylation of alkanes with olefins. By "discrete form," it is meant that the catalyst producing reaction is conducted in a manner that suppresses or eliminates the production of an acid-pair-hydrocarbon complex of a uncontrolled molecular weight in the range of a polymeric or tar mixture. The "discrete" catalyst produced is of a controlled molecular weight range and is soluble in the supercritical medium in which it is first generated or, if precipitated and recovered, is later redissolvable in such a medium.

Liquid Phase Operation

In liquid phase operation the catalyst may be conveniently prepared by dissolving the Lewis acid in a hydrocarbon liquid and thereafter, based upon the content of dissolved Lewis acid, adding appropriate quantities of Bronsted acid halide or Bronsted acid donor to the liquid. Alternatively the Bronsted acid halide or donor may be added to the isomerization or alkylation reactor with the hydrocarbon liquid having the dissolved Lewis acid being separately added to the reactor. The catalyst forms in the homogenous mixture in the reactor.

However formed, the catalyst complex is dissolved in the homogenous fluid medium in an amount that provides a catalyst concentration of from about 3.0 to about 22.5 millimoles per 1000 g of medium, measured as $MX_m$ where M is a Group 3a, 5a or 5b metal or metalloid, X is halide and "m" is an integer equal to the highest oxidation state of M. The homogenous fluid medium is maintained at a temperature sufficient to prevent precipitation of the catalyst complex from solution therein.

The Invention Processes

The invention catalyst may be utilized in two processes: the isomerization of alkanes; and the alkylation of isomerized alkanes with olefins.

a. The Isomerization Process

The isomerization process occurs readily when an alkane comprising from about 4 to about 12 carbon atoms is contacted with the invention catalyst. It is preferred that this contacting take place in a continuous flow reactor, for example a plug flow reactor. When the medium is a supercritical fluid pressure drop should be minimized to maintain supercritical fluid conditions and avoid catalyst precipitation.

Supercritical Fluid Operation

In the practice of the process with a supercritical fluid medium, an alkane comprising from 4 to 12 carbon atoms and a solvent if desired are first charged to a catalyst formation reactor, maintained at conditions so that its contents are in a supercritical fluid state, to produce the catalyst active for isomerization.

When the discrete catalyst has been produced, as described above, and it is desired to isomerize an alkane stream, then the catalyst formation reactor effluent (containing alkane, solvent if present, catalyst) is charged to the isomerization reactor. Further quantities of alkane to be isomerized and solvent may also be charged to the isomerization reactor, as long as a discrete catalyst concentration of from about 3.0 to about 30 millimoles per 1000 g of medium, expressed as a Lewis acid content. Preferably about 15 millimoles of Lewis acid per 1000 g of weight of alkane and solvent is maintained to achieve commercially useful reaction rates.

When a solvent is used the ratio of alkane:solvent in the reactor is preferably in the range 20:80 to 30:70, although other ratios may also be used, as long as super-critical fluid conditions are maintained. When, for example, the alkane is normal butane, the Lewis acid is $AlCl_3$, the Bronsted acid is HCl and the solvent is ethane, then the reactor should be maintained at a pressure of about 1,000 psia and the temperature should be about 200° F. (93° C.). While charging the hydrocarbon-solvent (normal butane-ethane in the ratio about 30:70) mixture to the isomerization reactor, a controlled quantity of HCl should be injected into the reactor to provide a proportion of HCl ranging from about 0.05 to about 0.22 mol. %, and preferably about 0.05 to about 0.1 mol. % based on the solvent.

On the other hand, if an olefin is to be isomerized, then the discrete catalyst is first produced in the formation reactor using an alkane as a reactant to complex with and form the catalyst species. This catalyst composition may then be injected into an isomerization reactor, into which a supercritical fluid mixture of olefin and solvent is charged. The ratio of olefin: solvent is most preferably from about 30:70 to about 20:80, as explained above. In the isomerization reactor all components become the homogenous medium within which the isomerization reaction proceeds. The discrete catalyst concentration is present in the range from about 3.0 to about 30 millimoles of Lewis acid per 1000 g of medium, preferably about 15 millimoles per 1000 g of olefin and solvent.

While residence times in the isomerization reactor will depend on many factors including amount of catalyst, acid-pair of catalyst, type of alkane or olefin charge, and desired single-pass conversion, the alkane or olefin to be isomerized should typically have a residence time sufficient to achieve a conversion approaching the thermodynamic equilibrium value in the isomerization reactor. This residence time should be at least about 5 minutes, preferably at least 8 minutes, and most preferably at least 10 minutes. Thus, the conversion from normal alkanes or olefins to isoalkanes or isoolefins, respectively, takes place in a relatively short time. Typical conversions can range up to the thermodynamic equilibrium conversion on a single pass through the reactor depending upon reactor conditions, actual catalyst used and the alkane or olefin being isomerized.

When isomerizing an olefin, the lowest practical temperature should be employed. This is so because the olefin is more reactive than the n-alkane component of the fluid and will isomerize to an isoolefin at temperatures at which the n-alkane does not isomerize. At low reaction temperatures then an alkylation reaction is avoided by preserving the n-alkane as in its n-alkane form, and an iso-olein product may be recovered.

The components of the effluent stream from the isomerization reactor, including isoolefins or isoalkanes and unreacted normal olefins or normal alkanes together with catalyst, solvent and any excess Bronsted acid, are then separated. The catalyst is readily precipitated by reducing the pressure to subcritical ranges. The residual separated normal alkanes or olefins are recycled back to the reactor inlet as is the solvent. The isomerized product may be diverted for other use, such as for alkylation with an olefin to produce an alkylate component stream for blending into motor gasolines.

Liquid Phase Operation

In liquid phase operation, the n-alkane to be isomerized is utilized as the fluid for the homogenous reaction medium. The homogenous reaction medium is formed by dissolving a quantity of Lewis acid in the n-alkane while simultaneously or subsequently adding in appropriate quantities of the Bronsted acid or Bronsted acid donor to the medium and, if desired, a transition metal halide catalyst modifier. This homogeneous medium is maintained in a reaction zone at a temperature of at least about 200° F. (93° C.), and preferably from about 200° F. to about 260° F. (93° to about 127° C.) and a pressure of from about 500 to about 650 psia for a time sufficient to achieve a conversion of n-alkane to isoalkane which approaches the thermodynamic equilibrium value. Generally the residence time of the homogeneous medium in the reaction zone should be at least about 30 minutes, preferably at least about 40 minutes. Following the reaction, the hydrocarbon content of the medium—unreacted n-alkane and product i-alkane—and the catalyst complex may be separated from each other by flashing the hydrocarbon content or by running the medium through a bed of absorbent for the catalyst after reducing the temperature of the medium. A bed of gamma or eta alumina would serve as an absorbent for the catalyst.

b. The Alkylation Process

The alkylation process may be carried out as a secondary step after isomerization with the invention catalyst or may be carried out in the same reactor. Both the isomerization and alkylation reactions are exothermic, especially the alkylation reaction. Consequently, heat removal capability is a factor in reactor design selection. It may also be desirable to practice the isomerization and alkylation reactions at two different temperatures.

Supercritical Fluid Operation

As explained above, the product from the isomerization of alkanes contains the isoform of the alkane together with discrete catalyst, solvent and any excess Bronsted acid. Since the invention catalyst is highly active for the alkylation of isoalkanes, it is advantageous to add an olefinic composition to the effluent product of the isomerization reactor. Consequently, one embodiment of the invention provides a reactor which combines isomerization of alkanes and subsequent alkylation. The charge to the reactor passes through an initial isomerization zone and the effluent from this zone is discharged into an alkylation zone. Another embodiment uses two separate reactors.

The isomerization zone of the reactor for converting normal alkanes to isoalkanes has been described above. It has been found that when the pressure on the isomerization reactor effluent is dropped to below the pressure required to maintain supercritical fluid conditions, then the catalytic composition may no longer be soluble in the solvent so that the discrete catalyst precipitates from the hydrocarbon-solvent mixture. Therefore, it is desirable that the step of transferring isomerization reactor effluent and the alkylation zone of the reactor itself be designed for a negligible pressure drop.

A suitable alkylation reactor design is an empty vessel having approximately the same or slightly larger diameter than the isomerization reactor so that little, if any, pressure drop takes place when the product of the isomerization reactor is discharged into the alkylation reactor. In one embodiment, the isomerization and alkylation reactors may both be contained within a single conduit. Alternatively, they may be separate reactors.

An olefin feed wherein the olefin comprises from about 3 to about 9 carbon atoms is charged to the alkylation reactor, preferably either at an entry point near the entry of the isomerization reactor effluent into the alkylation reactor or, more preferably, at a multiplicity of points along the alkylation reactor's length. The proportion of olefin:alkane feed supplied should be in the ratio from about 1:2 to about 1:20 in the charge to the alkylation reactor. Preferably, the ratio of olefin to alkane should be from about 1:5 to about 1:15, most preferably about 1:8.

Upon addition of the olefin, alkylation proceeds and the process produces an alkylate that has a low conjunct polymer or tar content relative to typical alkylates from the HF acid or sulfuric acid processes. To achieve this, the discrete catalyst should be present in a concentration ranging from about 3.0 to about 30 millimoles of Lewis acid per 1000 g of medium, preferably 15 millimoles, based upon the weight of the isoalkane and solvent. Further, to minimize halogenation of the alkylate, excess Bronsted acid should be minimized as far as possible.

Residence time of the medium with added olefin in the alkylation reactor should be at least about 1 minutes, preferably at least about 2 minutes to achieve a useful conversion to alkylate. If both isomerization and alkylation is to take place in the same reactor, then the isomerization step is rate controlling since it is the slower of the two reactions. Therefore, reactors carrying out both processes should be sized for isomerization kinetics and should have preferable residence times of about 8 minutes, most preferably at least 10 minutes.

Conversion of olefin to alkylate is high and, depending upon the particular catalyst used, and the particular isoalkanes and olefins, ranges up to 95-100% on a single pass. Thus, for the preferred isobutane, in the presence of a catalyst obtained from the $AlCl_3$/HCl acid pair and normal butane, ethane solvent, reacting with olefins having from 3 to 9 carbon atoms can provide conversion of olefin of up to about 100% on a single pass.

Of course, if the alkylation process is not continuously coupled with a prior isomerization process, and alkylation alone is practiced, the homogenous reaction medium will be formed with an isoalkane and solvent mixture which is brought to supercritical fluid conditions and made to contain dissolved Lewis acid to which simultaneously or subsequently the Bronsted acid or donor is added. This homogenous medium is then fed to an alkylation reactor to which olefin is admitted in a quantity to produce an isoalkane to olefin mole ratio of from about 1 to about 10. The contact of olefin with the homogeneous medium preferably is conducted across a quiescent interface. Olefin enters the homogenous medium by molecular diffusion and the alkylation reaction occurs within the medium. Competing reactions which would produce undesirable polymer and tar by-product, which otherwise would occur in the olefin phase are minimized or eliminated since the olefin phase does not contain any appreciable content of catalyst since this remains dissolved in the homogenous reaction medium. The very high transient or local isoalkane to olefin ratio existing in the homogenous mixture by reason of the molecular diffusion of olefin into the homogenous medium promotes alkylation and further minimizes production of undesired by-products.

Liquid Phase Operation

In this mode of operation the fluid of the reaction medium may comprise the hydrocarbon effluent from a prior isomerization reaction, a mixture of n-alkane and iso-alkane, or in an alkylation alone process, just the isoalkane. If the fluid is an isomerization effluent it may already contain sufficient dissolved Lewis acid-hydrocarbon complex catalysts to accomplish the desired alkylation reaction when olefin is brought into contact with this medium. Otherwise, the fluid may be used for forming a homogenous medium containing a desired quantity of dissolved catalyst complex by any of the procedures heretofore described and the medium then placed in a reaction zone where it is maintained at a temperature of at least about 140° F. (60° C.) while under a pressure of from about 250 to about 450 psia. Thereupon, contact of this medium with an olefin in a quantity to provide a mole ratio of alkane to olefin of from about 1 to about 10 will produce the alkylation reaction. Residence time of the medium and olefin within the reaction zone is preferably long enough to permit complete reaction of the quantity of olefin admitted to the zone. Preferably the residence time is at least 7 minutes, more preferably at least about 10 minutes. Following the completion of reaction the hydrocarbon and catalyst content of the medium may be separated from each other by any technique as heretofore described.

An Embodiment of the Invention Isomerization and Alkylation Process Flow

Supercritical Fluid Operation

The invention catalyst system may be utilized in any of a wide variety of process flow schemes in order to produce either an isomerized product or an alkylate product. Illustrative of the variety of process flows, is the simplified flow scheme illustrated in FIG. 1. In this flow scheme, fresh alkane 102 combines with a compressed charge 104 including recycled butanes 100, a compressed recycled solvent stream 128 and solvent make-up stream 103, to produce catalyst dissolver feed 106 which is charged to the catalyst dissolver 110 which is maintained at supercritical conditions. Also charged to the dissolver 110 is a controlled quantity of makeup catalyst via conduit 112.

Make-up catalyst is produced in the "catalyst formation" or "make-up catalyst" reactor 180 which permits contact between an alkane/solvent stream 184 (shown as a slip stream taken from total fresh alkane charge 101) with the solid Lewis acid and, if desired a transition metal halide modifier. To the stream 112 exiting reactor 180 is added a charge of Bronsted acid via line 182. This contacting step produces the invention catalyst which is soluble in the solvent under supercritical conditions. Further, the reactor 180 is a continuous flow reactor in that reactants and products flow through the reactor, with minimal pressure drop, and is designed for a residence time of less than about 5 minutes, preferably less than 3 minutes. Within these constraints, the reactor may be of any of a variety of designs. In one of the preferred designs, the reactor may be constructed like a conventional one tube pass shell and tube heat exchanger with the Lewis acid and transition metal packed within the tubes in such a manner that the pressure drop through the tubes is minimal so that supercritical conditions may be maintained throughout the length of the tube. Thus, the reactants will flow into the tube side of the reactor, flow along the tubes to allow reaction with the Lewis acid and transition metal. Unreacted alkane, solvent, and catalyst flow from the exit end of the tubes into a collection header where the Bronsted acid is added and thence to dissolver 110. On the shell side of the catalyst formation reactor 180, a heat exchange fluid may be introduced in order to maintain the temperature within the desired operating range, since the catalyst formation reaction is exothermic.

The make-up catalyst provided via conduit 112 from the catalyst formation reactor 180 is sufficient to offset losses in the process and the formation reactor may be operated continuously or only intermittently, as needed.

Catalyst dissolver 110 contains discrete catalyst which has previously been recovered as a precipitate. This catalyst is dissolved into the supercritical fluid dissolver charge, which comprises the fluids in lines 106 and 112, up to the desired concentration of discrete catalyst relative to alkane and solvent. This may readily be achieved by bypassing a proportion of the charge via line 108 around the dissolver 110. The effluent from dissolver 110, now containing a useful amount of dissolved discrete catalyst, flows via conduit 113 to the isomerization reactor 115.

Isomerization reactor 115 is designed for ease of heat removal since the reaction is exothermic and should further be designed to minimize pressure drop to maintain supercritical fluid conditions. Within those restraints, many designs are possible. The simplest design is a conduit, forming a plug flow reactor, surrounded by a means for transferring heat from the conduit. Thus, a shell and tube design wherein reaction takes place on the tube side and heat is carried away by a cooling medium on the shell side, may be employed. The isomerization reactor should have a residence time sufficient to allow significant conversion of alkanes to isoalkanes. The invention catalyst allows conversions to approach the thermodynamic equilibrium conversion.

The effluent from reactor 115, containing the isomerized form of alkanes, unreacted alkanes, solvent, and any excess Bronsted acid, flows into exit conduit 114 which is equipped with a T-piece one end of which is the inlet to an alkylation reactor 116 and the other end of which is connected to a line 118 which carries olefin feed for the alkylation reaction. As mentioned before, the olefinic feed component desirably comprises olefins having from 3 to about 9 carbon atoms.

The alkylation reactor 116 should be designed for minimal pressure drop and should provide a sufficient residence time for the alkylation reaction to take place to the desired level of isoalkane reaction. Within these constraints, the alkylation reactor could have any of a variety of designs. One example of such a design is a simple plug flow reactor which has the appropriate volume to provide the desired residence time and which has means for removing heat of reaction. Provisions should be made for addition of olefin at several points, preferably 3–5, along the length of the reactor. Thus, the reactor may comprise a conduit calculated to provide the appropriate residence time at design flow rates.

The effluent from the alkylation reactor 116 is led by a pipeline 120 to the inlet of a catalyst "precipitator" 122. This vessel is desirably of the same configuration as the catalyst dissolver 110. Thus, the charge to the precipitator is passed through the tubes while pressure is reduced to below supercritical conditions. Under these conditions, the catalyst precipitates in the precipitator 122. Thus, catalyst contained in "dissolver" 110 is gradually transferred to "precipitator" 122. When the catalyst is substantially exhausted from dissolver 110, the flow through the process system may be reversed by suitable piping, valving and control design so that vessel 122 becomes the "dissolver" while vessel 110 becomes the "precipitator."

The effluent from precipitator 122, which is essentially free of catalyst and at below critical pressure, is charged via line 124 to a solvent rerun tower 126. In the rerun distillation column 126, the solvent, preferably propane, and any residual Bronsted acid is separated from the unreacted olefin or alkane feed and the alkylate product. The solvent is removed as an overhead product in line 128 and is charged to the inlet of a pump 130 for recycling to the inlet of the isomerization reactor 110, through line 104. The bottom product of the rerun tower 126, containing alkylate, unreacted alkanes or olefins, and a small amount of residual Bronsted acid is charged via line 132 to a depropanizer 134. This depropanizer distillation column 134 separates light ends, in particular propane and propene, from the alkylate and unreacted alkanes and olefins. The propane-propene stream is removed in the depropanizer overheads via line 136, is cooled and condensed in cooler-condenser 138, and then flows to a caustic scrubber 139 for the removal of any residual trace amounts of acid. The effluent via line 140 from the caustic scrubber, now free of residual acid, may be used in other chemical processes or as a source of fuel. The bottom product 142 of depropanizer 134 is charged to a debutanizer 144 which removes butanes as an overhead product in line 100 for charging to the suction of pump 130 and thence recycled to the front end of the isomerization reactor 110. The bottom product 146 of the debutanizer 144 is treated to remove any residual Bronsted acid or alkyl chlorides in scrubber 148. The essentially acid-free effluent from caustic scrubber 148 is charged by line 150 to an alkylate splitter 152. The alkylate splitter separates the alkylate stream into a light alkylate overhead product 154 and a heavy alkylate bottom product 156. The heavy alkylate product 156 is then optionally charged to a alkylate flash drum 158 for separation into an overhead heavy alkylate 160 and a heavy tower bottom product 162.

The light alkylate stream 154 and the heavy alkylate product 160 are readily blended into gasoline, providing a high octane blending component that may be substituted for aromatic components.

While the simplified flow diagram of FIG. 1 shows the basic flow scheme, those of ordinary skill in the art will readily appreciate the additional equipment and modifications that may be necessary in practice.

As explained above, the invention catalyst and process may be carried out in any one of a variety of reactor designs. The reactor design is essentially only restricted by the functions that it is required to perform. For example, the reactor should be capable of withstanding supercritical reaction conditions. Further, the reactor should be of such a design as to minimize pressure drop so as to maintain the supercritical fluid containing the active catalyst above the critical pressure to avoid precipitation of the catalyst. Further, the design is desirably of a type that permits ease of removal of heat of reaction. Consequently, the shell and tube variant is preferred.

Figure 2:
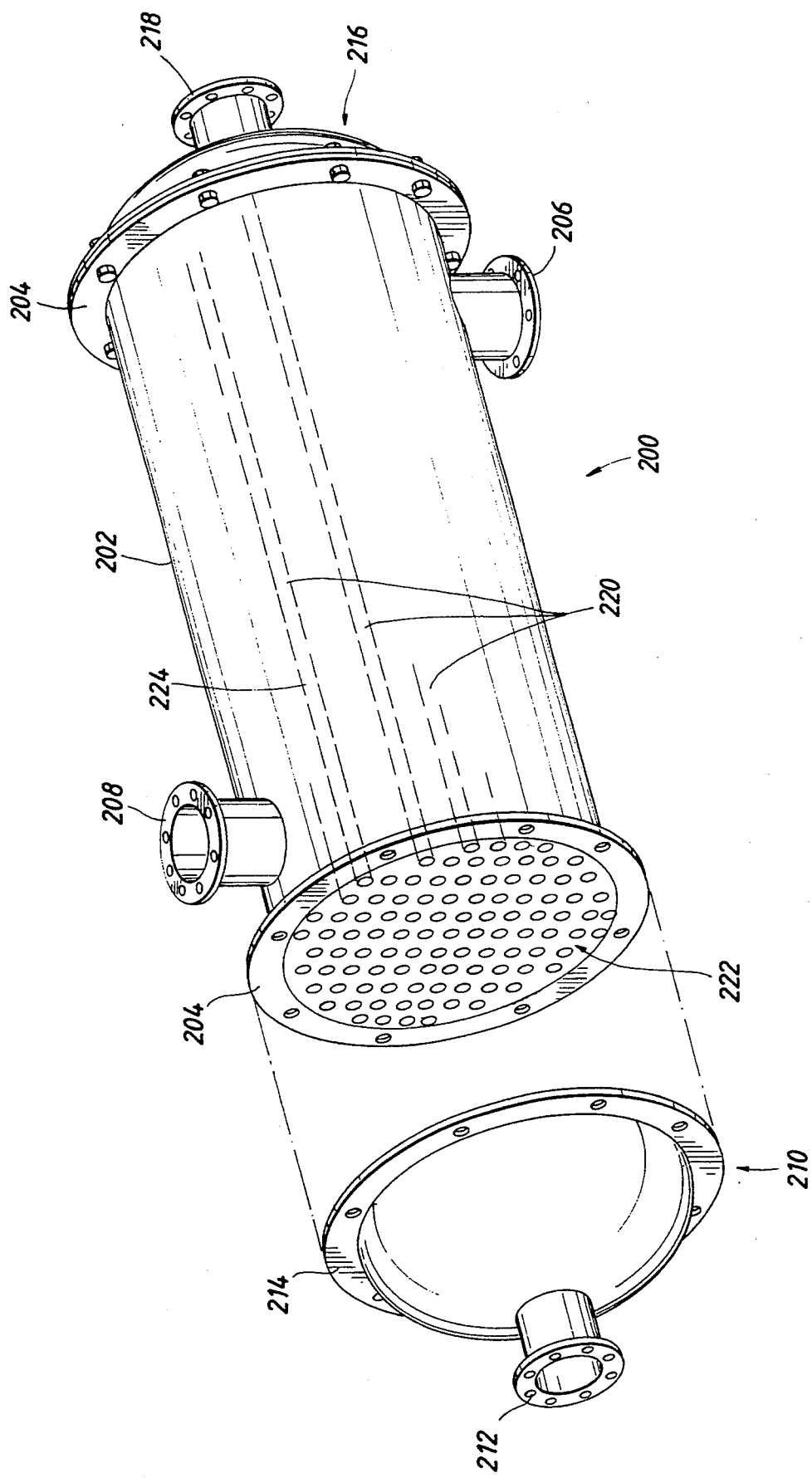
FIG. 2 is a schematic representation of an embodiment of a reactor useful in the invention process.

FIG. 2 illustrates, schematically, a reactor of the shell-and-tube-type design. The reactor 200 has a cylindrical shell 202 with flanges 204 at each end. Further, the shell is fitted with an inlet port 206 and an outlet port 208 for allowing a heat exchange fluid to travel through the shell of the reactor 200. Thus, the space within the shell surrounding the tubes provides a means for heat exchanging the tubes. An inlet bonnet 210 fitted with an inlet port 212, for receiving a charge of reactants, and a flange 214 is bolted to the flange 204. Similarly, an exit bonnet 216 is bolted to flange 204 at the exit end of the shell and is supplied with an exit port 218, for discharging reaction products from the reactor. The shell 202 contains a tube bundle 220. This tube bundle has an inlet header plate 222 through which tubes 224 extend and connect with exit header. The headers fit tightly within the shell so that a supercritical fluid cannot pass from the tube side to the shell side, or vice versa.

In practice, to produce a catalyst formation reactor, the tubes would be filled with a Lewis acid and transition metal or a packing with Lewis acid and transition metal distributed upon its surface. The reactor charge would enter at the inlet port 212, flow through the tube bundle 224, thereby contacting the Lewis acid and transition metal and forming the catalyst, before exiting via exit port 218. At the same time, a coolant fluid would be charged through inlet port 206, flow over the tube bundle, thereby removing the exothermic heat of catalyst formation, and exit via exit port 208.

As explained, the reactor may also be used to dissolve the catalyst into a supercritical fluid stream or precipitate the catalyst from an alkylate or an isomerized product stream onto the inner surface of the tubes or onto a packing placed within the tubes. In this manner, the vessel functions as either a "dissolver" or a "precipitation" vessel.

To produce either an alkylation or an isomerization reactor the tubes would not be filled with Lewis acid, transition metal, or with packing but would preferably be left empty to minimize pressure drop.

Liquid Phase Operations

Figure 4:
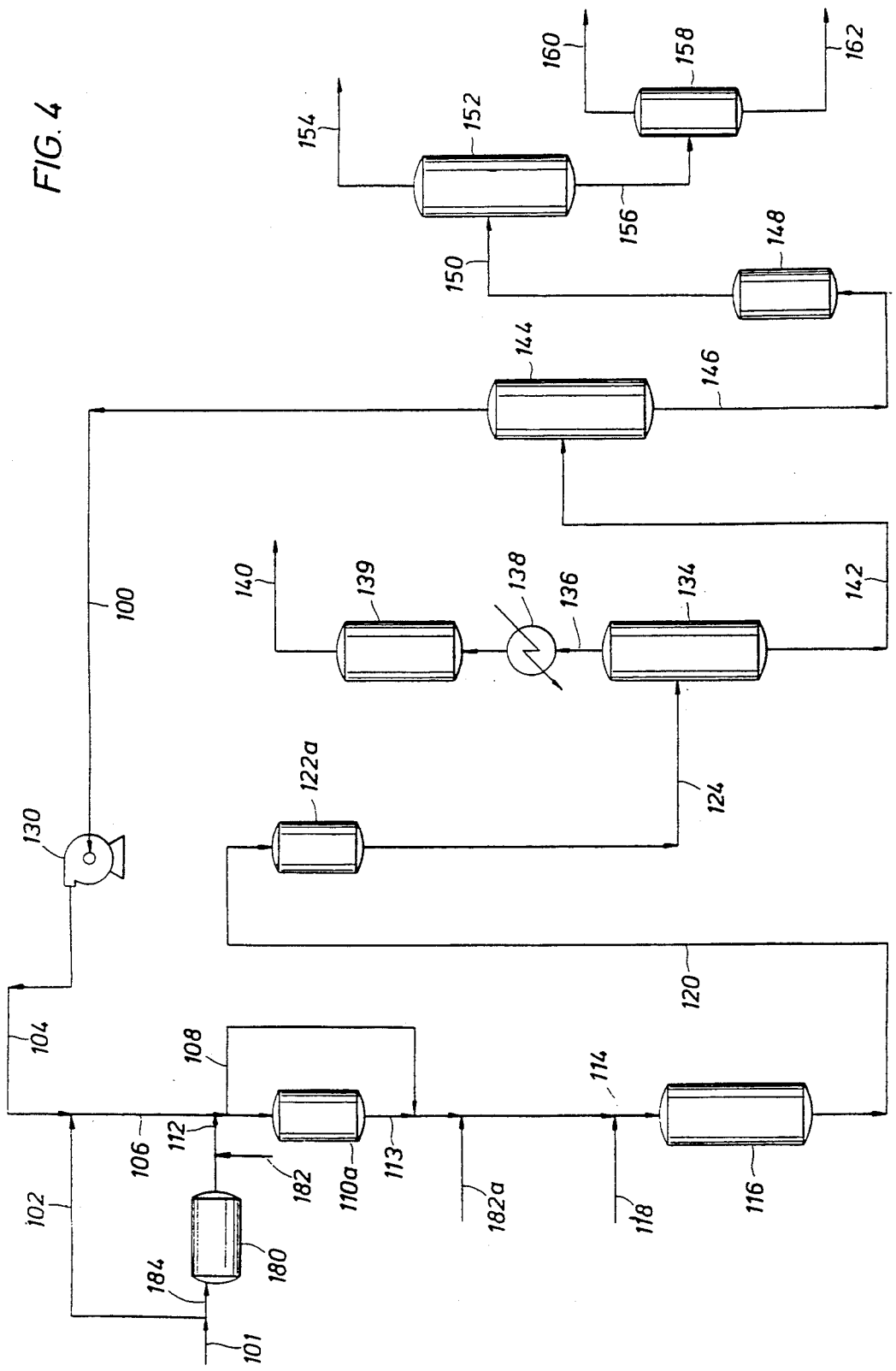
FIG. 4 shows a flow diagram for an embodiment of the invention wherein the process is practiced under liquid phase conditions.

Operations would be conducted in a similar flow manner but at conditions of temperature and pressure to preserve the alkane in a liquid state. FIG. 4 illustrated a flow scheme for a liquid phase alkylation process. In many respects the flow scheme is similar to that for supercritical fluid operation like in FIG. 1, differing therefrom mainly by the deletion of equipment items which are needed only for supercritical fluid operation and altering the service duties of other vessels. Accordingly in FIG. 4, equipment items which service identical functions are identically numbered, equipment which services an altered function is numbered with an "a" suffix. In liquid phase operation vessel 110a is loaded with Lewis acid, and Bronsted acid is added by line 182a. Following the alkylation reaction in reactor 116 the alkylate product stream 120 is fed to vessel 122a in which is located an absorbant for removal of the catalyst, after which the alkylate product is fed by line 124 to the remainder of the process, the operations of which are the same as previously described.

The following examples are illustrative of the invention and do not in any way limit or define the scope of the invention.

EXAMPLES

Description of Apparatus Used in the Examples

Figure 3:
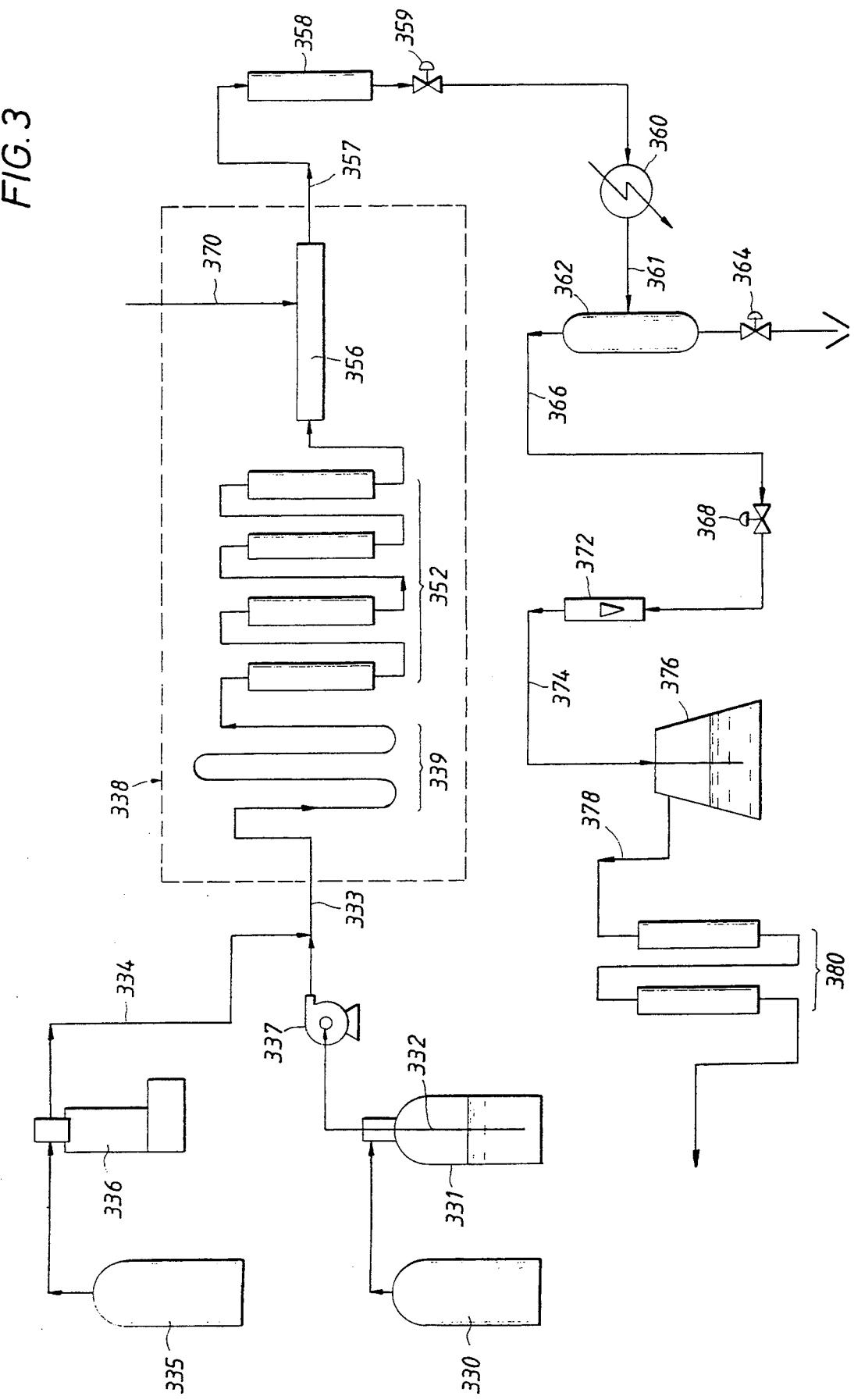
FIG. 3 shows a flow diagram of the apparatus used in the examples.

All examples 1–3 of supercritical fluid operations were produced on the apparatus illustrated schematically in FIG. 3. In FIG. 3, the alkane to be isomerized is contained in a pressure vessel 331 and solvent, in the gaseous state, from pressure vessel 330 is added to pressure vessel 331 by bubbling into the alkane through a dip tube 332 until the pressure in 331 reaches about 200 psi. This bubbling step takes place over about 48 hours and the resultant fluid mixture is charged to the suction of charge pump 337. The protic Bronsted acid is held in vessel 335 and is drawn into a syringe pump 336 with a piston volume of about 500 ml, when fully extended. When the piston is raised, the Bronsted acid is compressed and liquified into a volume of about 50 ml at a pressure of about 1300 psi. This compressed Bronsted acid flows via tube 334 into tube 333, the discharge of charge pump 337, which carries the mixture of solvent and alkane into the reactor system, which is contained within a constant temperature bath 338 through which ethylene glycol is circulated to maintain the desired temperature level in the reactor system.

In the reactor system, the feed 333 to the reactor system first passes through about 20 feet of preheated tubing 339 to bring the feed up to the operating temperature. The feed mixture then enters a series of four tubes 352, the middle two tubes containing a Lewis acid of the metal halide-type and a transition metal. In these middle tube reactors 352 the protic Bronsted acid, alkane, Lewis acid, transition metal if desired and solvent interact under supercritical fluid conditions to produce the invention discrete catalyst dissolved in a homogenous medium for the isomerization and alkylation of alkanes and olefins. The first and last of tubes 352 are filled with alumina to form a first and last "guard chamber." From these catalyst formation and guard tubes 352, the supercritical fluid mixture proceeds to the inlet of a reactor 356 where isomerization and alkylation, if desired, takes place. If alkylation is desired, olefins are added via line 370, located about two-thirds the length of the reactor 356 from its inlet. The isomerized alkanes, residual unreacted alkanes, solvent, catalyst, and residual Bronsted acid exit from the reactor 356 through line 357 and enters a tube 358 filled with magnesium oxide to remove residual Lewis acid from the effluent.

Essentially Lewis acid-free effluent passes from tube 358 through pressure reducing valve 359, and is partially liquified. The partial liquid phase effluent then enters condenser 360 which liquifies at least the alkylates ($C_5$ and higher) in the effluent. This partially liquified effluent exits the condenser in line 361 and is separated in separator 362 into a liquid product and a vapor product. The liquid product may be periodically removed by opening valve 364. The vapor product flows via line 366 through valve 368 to a rotameter 372, which measures its flow rate. The vapor product exits the rotameter 372 in line 374 and flows to a scrubber 376 containing 10 wt.% caustic for removing residual Bronsted acids. From the scrubber 376, the essentially acid-free effluent flows via line 378 to driers 380 and thence to sample collection.

The examples that follow were carried out on the above described apparatus.

EXAMPLE 1

Effect of Residence Time on Supercritical Fluid Conversion of Alkanes to Isoalkanes Using the apparatus of FIG. 3, a feedstream comprising normal butane as the alkane, ethane as the solvent, HCl as the Bronsted acid, was prepared and charged to reactors 352 containing $AlCl_3$ as the Lewis acid. The reactor system was charged to 1000 psia and the temperature of the system was maintained at 200° F. (93° C.) using the ethylene glycol constant temperature bath. Residence time was calculated based on a fluid density of 0.1 g/cc. The concentration of HCl was controlled by controlling the feed syringe pump 336.

In a first run, the feed and product compositions were as shown in Table I, for an isomerization reactor residence time of 0.55 minutes. In a second run, residence time was increased to 5 minutes and conversion increased to 1.6 times that of the first run, as can be see in comparing Table II with Table I. All gas compositions are shown on an HCl-free basis.

TABLE I

| | | | Gas Composition Mole % | |
|---|---|---|---|---|
| | | | Feed | Product |
| N-butane Rate | 59.5 | cc/hr | Ethane 76.8 | 80.6 |
| HCl Rate | 5.9 | cc/hr | N-butane 23.2 | 11.6 |
| Catalyst Formation Reactor Residence Time | 3.5 | min | I-butane — | 7.8 |
| Guard Bed Residence Time | 3.5 | min | | |
| Isomerization Reactor Residence Time | 0.55 | min | | |

TABLE II

| | | | Gas Composition Mole % | |
|---|---|---|---|---|
| | | | Feed | Product |
| N-butane Rate | 71.3 | cc/hr | Ethane 71.8 | 72.1 |
| HCl Rate | 7.4 | cc/hr | N-butane 28.2 | 10.1 |
| Catalyst Formation Reactor Residence Time | 3.5 | min | I-butane — | 16.7 |
| Guard Bed Residence Time | 3.5 | min | | |
| Isomerization Reactor Residence Time | 5 | min | | |

The foregoing illustrates the importance of allowing sufficient residence time for the isomerization reaction to obtain a high conversion of normal alkanes.

EXAMPLE 2

Comparison of Supercritical and Liquid Phase Isomerization

Using the apparatus of FIG. 3, butane feed was subjected to supercritical isomerization using ethane as a solvent, $AlCl_3$ as the Lewis acid, iron as the transition metal, and HCl as the Bronsted acid. During the supercritical phase isomerization, ethane was fed at 0.25 gram moles per minute, butane at 0.008 gram moles per minute and HCl concentration was maintained at 4.8 mol % relative to the ethane solvent and butane. Temperature was maintained at 200° F. (93° C.) and pressure at 1000 psia. Residence time in the reactor was about 1.7 minutes based on an assumed fluid density of 0.1 g/cc and a butane conversion of 55% was achieved.

After about 3.5 hours of stable supercritical operation, the ethane was excluded from the system and its concentration in the effluent declined to zero in about two hours. Isomerization in liquid phase butane was then obtained. The liquid phase conversion was observed to be about 35%, and decreasing with time. The fluid density of liquid butane is about 0.579 g/cc so that the residence time in the entire reactor system was calculated at 39.4 minutes. Further, assuming first order reaction kinetics, it is estimated that the liquid phase reaction rate is at least 50 times slower than the rate at supercritical conditions.

EXAMPLE 3

Supercritical Fluid Alkylation of Butene With Normal Butane

A combined isomerization and alkylation process was conducted using the apparatus of FIG. 3 at the conditions listed below:

| Operating Conditions | |
|---|---|
| Condition | Numerical Value |
| Pressure | 1000 psia |
| Temperature | 180° F. (82° C.) |
| Normal Butane Rate | 42.7 cc/hr |
| Butene Rate | 6.5 cc/hr |
| Catalyst Formation Residence Time | 3.5 min. |
| Isom Reactor Residence Time | 3.5 min. |
| Alkylation Reactor Residence Time | 0.6 min. |
| HCl Rate | 0.34 cc/hr |

The overall composition of the supercritical fluid charged to the reactors was as follows:

| Component | Percentage Mole % |
|---|---|
| Ethane | 81.1 |
| N-Butane | 15.9 |
| Cis-2-butene | 0.9 |
| Trans-2-butene | 1.7 |
| HCl | 0.4 |

The ethane, N-butane and HCl were passed through the catalyst formation reactor and isomerization reactor prior to the addition of the olefin at the inlet to the alkylation reaction zone. Samples of the liquid and gaseous product were collected and analyzed. From these analyses, the liquified product includes mainly unidentified isomers of hydrocarbons typically having less than 14 carbon atoms. Of the paraffin and olefins produced 46% were alkylate paraffins. An analysis of the liquid product was as follows:

| Liquid Product Analysis | Wt. % of liquid |
|---|---|
| Alkylate Paraffins | |
| $C_7$ | 0.2 |
| $C_8$ | 4.0 |
| $C_{10}$ | 0.5 |
| Alkyl Chlorides | |
| $C_4$ | 2.8 |
| $C_5$ | 1.7 |
| $C_8$ | 5.4 |
| Olefins | |
| $C_8$ | 1.5 |
| $C_9$ | 2.5 |
| $C_{10}$ | 0.8 |
| $C_{13-14}$ | 0.8 |
| Dissolved Butane | 0.8 |
| Total Identified | 21.0 |

| Gaseous Product Analysis | Mole % |
|---|---|
| Ethane | 87.0 |
| n-butane | 10.4 |
| i-butane | 1.1 |
| cis-2-butene | 0.2 |
| trans-2-butene | 1.3 |

From the product gas analysis it is noted that butene conversion was about 20% and that i-butane had been formed.

EXAMPLE 4

Liquid Phase Alkylation Procedure

All the catalyst preparation steps are conducted under a dry nitrogen atmospheres.

A 250 mL 3-necked round-bottom flask is equipped with a magnetic stirring bar, dropping funnel, water-cooled condenser, a thermometer, and under a positive nitrogen atmosphere. Place 9.7 g of diisobutylaluminum chloride in the dropping funnel. Place 7.9 g of aluminum chloride and 200 ml (132 g) dried n-hexane in the round-bottom flask. Slowly add the diisobutylaluminum chloride to the flask with stirring. Allow the mixture to be stirred for 24 hours. The mixture is filtered with a pressurized filter. The filtrate is analyzed for aluminum content. Aluminum analysis: 1.8%, experimental: 1.9% theoretical. The n-hexane solution contains about 10.3% monoisobutylaluminum dichloride (MIBAD) catalyst precursor.

An i-butane feed consisting of 0.14 wt. % of 1-chlorobutane was fed into the reactor unit at a rate of 96 cc/hr. A separate i-butane blend consisting of 2.5 wt. % i-butyl $AlCl_2$ and 22.5 wt. % n-hexane was fed at a rate of 7.8 cc/hr and mixed with the other stream at the operating conditions of 220° F. (104° C.) and 650 psig.

2-butene was added to this stream at a rate of 4.5 cc/hr. The total feed stream passed through a 4 foot long ¼ inch OD reactor tube before depressuring across a metering valve. The residence time is about 10 minutes. The concentration of the catalyst in the entire stream was 1550 wppm expressed as $AlCl_3$. Analysis of the exit stream showed 100% olefin conversion. The exit stream flowed into a coldtrap at $-110°$ F. ($-79°$ C.). The liquid collected in the coldtrap was allowed to warm to ice water temperature and the liquid was analyzed. The GC/MS analysis of the liquid is as follows:

| | Wt % |
|---|---|
| propane | 1.1 |
| isobutane | 8.7 |
| n-butane | 0.3 |
| isopentane | 3.4 |
| 2,3-dimethylbutane | 4.6 |
| 2-methylpentane | 3.6 |
| 3-methylpentane | 0.4 |
| n-hexane (from the catalyst blend) | 14.9 |
| 2,4-dimethylpentane | 4.3 |
| 2,3-dimethylpentane | 2.1 |
| 2,2,4-trimethylpentane | 11.5 |
| 2,5-dimethylhexane | 6.0 |
| 2,4-dimethylhexane | 4.8 |
| 2,3,4-trimethylpentane | 6.9 |
| 2,3,3-trimethylpentane | 4.0 |
| 2,3-dimethylhexane | 3.1 |
| 2,-methylheptane | 1.6 |
| 3-methylheptane | 1.0 |
| 2,2,5-trimethylhexane | 4.0 |
| 2,3,5-trimethylhexane | 1.5 |
| n-nonane (internal standard) | 10.4 |
| unidentified hydrocarbon | balance |

EXAMPLE 5

Supercritical Fluid Alkylation

Ethane was fed into the reactor unit at a rate of 165 cc/hr. A separate feed stream consisting of 96.3 vol % ethane and 3.7 vol. % HCl was added to the ethane at a rate of 2.5 cc/hr. An i-butane feed of 50 cc/hr was also added to the ethane stream. The operating conditions were 180° F. (82° C.) and 1000 psig. This stream passed through a bed of AlCl3. A feed of 2-butene at a rate of 3.4 cc/hr was added to the stream of ethane, i-butane, HCL, and AlCl3. The entire stream has a calculated critical temperature (Li, C. C. *Can. J. ChE.* 19:709 (1972)) of approximately 130° F. and a calculated critical pressure (Reid, Prausnitz, and Poling, *The Properties of Gases and Liquids*, p. 131, (1987)) of 820 psia. This stream passed through 11 inches of ¼ inch OD tubing (reactor) before exiting across a metering valve. The residence time in the reactor was 30 seconds. The concentration of catalyst in the stream was approximately 1090 wppm as AlCl3. The outlet stream passed through a gas/liquid separation system with the gas being vented off and the liquid collected in an accumulator submersed in an ice bath. Analysis of the gas indicated 100% conversion. GC/MS analysis of the liquid is as follows:

|  | Wt % |
| --- | --- |
| Isobutane | 2.7 |
| isopentane | 2.6 |
| 2,3-dimethylbutane | 3.6 |
| 2-methylpentane | 2.4 |
| 2,4-dimethylbutane | 1.2 |
| 2-methylhexane | 2.0 |
| 2,3-dimethylpentane | 3.4 |
| 3-methylhexane | 1.3 |
| 2,2,4-trimethylpentane | 11.5 |
| 2,5-dimethylhexane | 8.4 |
| 2,4-dimethylhexane | 6.9 |
| 2,3,4-trimethylpentane | 6.5 |
| 2,3,3-trimethylpentane | 5.0 |
| 2,3-dimethylhexane | 2.3 |
| 2-methylheptane | 1.2 |
| 3-methylheptane | 1.2 |
| 2,2,5-trimethylhexane | 10.7 |
| 2,3,5-trimethylhexane | 0.8 |
| 2,6-dimethylheptane | 0.6 |
| 2,5-dimethylheptane | 0.9 |
| unidentified hydrocarbon | balance |

EXAMPLE 6

Fluid Phase Alkylation

The operating conditions were 200° F. (93° C.) and 650 psig. A propane feed containing 0.27 wt. % 1-chlorobutane was fed into the unit at 165 cc/hr. A i-butane stream was mixed into the propane stream at a rate of 40 cc/hr. A separate stream of i-butane passed through a bed of AlCl3 before mixing with the propane and butane stream. 2-butene was fed at a rate of 4.5 cc/hr to the entire stream. The stream had a calculated critical temperature of 220° F. (104° C.) and a calculated critical pressure of 620 psi. The critical temperature and critical pressure were calculated using the same method as in Example 5.

This stream passed through 1 foot of ¼ inch OD tubing (reactor) before depressuring at the metering valve. The residence time in the reactor was around seconds. The catalyst concentration was approximately 700 wppm as AlCl3. Gas analysis of the exit stream indicated about 80% olefin conversion. The gas/liquid separation system is the same used in Example 5. GC/MS analysis of the liquid is as follows:

|  | Wt % |
| --- | --- |
| isobutane | 3.5 |
| n-butane | 0.4 |

-continued

|  | Wt % |
| --- | --- |
| trans-2-butene | 1.2 |
| cis-2-butene | 1.2 |
| isopentane | 2.1 |
| n-pentane | 0.3 |
| 2,3-dimethylbutane | 1.0 |
| 2-methylpentane | 1.7 |
| 3-methylpentane | 0.9 |
| n-hexane | 0.5 |
| 2-chlorobutane | 0.8 |
| 2,4-dimethylbutane | 4.9 |
| 2-methylhexane | 3.1 |
| 2,3-dimethylpentane | 5.3 |
| 3-methylhexane | 2.2 |
| 2,2,4-trimethylpentane | 2.8 |
| 2,5-dimethylhexane | 4.5 |
| 2,4-dimethylhexane | 2.8 |
| 2,3,4-trimethylpentane | 1.5 |
| 2,3,3-trimethylpentane | 1.1 |
| C8-ane | 1.7 |
| 2-methylheptane | 0.2 |
| 3-methylheptane | 1.3 |
| 2,2,5-trimethylhexane | 1.1 |
| C9-ane | 0.9 |
| unidentified hydrocarbons | balance |

EXAMPLE 7

Liquid Phase Alkylation Using a Tubular Reactor

From a continuous operation, more than 700 grams of unstabilized alkylate (i.e. containing dissolved i-butane) was produced. The operating procedure was generally as described in Example 4. The operating conditions were as follows: T=220° F., P=650 psig, 2-butene feedstock, 2-butene/monoisolbutyl aluminum dichloride (MIBAD) molar ratio =65, i-butane/2-butene molar ratio =25, 1-chlorobutane/MIBAD =0.96, residence time of 9.5 minutes. The unstabilized alkylate was distilled. Product distribution is shown below:

| FRACTION NAME | BOILING POINT, °F. | | WEIGHT g | WEIGHT % |
| --- | --- | --- | --- | --- |
|  | INITIAL | FINAL |  |  |
| 1. Isobutane | NA | 20 | 178.0 | 31.1 |
| 2. C5 | 20 | 104 | 17.4 | 3.0 |
| 3. Light | 104 | 330 | 235.6 | 41.2 |
| 4. Heavy | 330 | 410 | 93.7 | 16.4 |
| 5. Residue | 410+ | NA | 46.9 | 8.2 |
| TOTAL |  |  | 571.6 | 99.9 |

Fraction 1 is dissolved i-butane, Fraction 2 is normal and isopentane. Fraction 3 is $C_6$ through $C_9$. Fraction 4 is $C_{10}$ through $C_{12}$. Fraction 5 is $C_{12+}$ residue. The light and heavy alkylates were analyzed in Research and Motor Octane engine tests to determine Research Octane Number (RON) and Motor Octane Number (MON). Results are shown below:

|  | BLEND | | BLENDING | | NEAT |
| --- | --- | --- | --- | --- | --- |
|  | RON | MON | RON | MON | RON |
| LIGHT ALKYLATE | 95.7 | 91.1 | 97.8 | 86.0 | 96.6 |
| Heavy alkylate | 94.6 | — | 93.4 | — | — |

BLEND octanes were determined for blends of 75 percent (volume) reference alkylate and 25% (volume) of experimental alkylate. Reference alkylate had a 95 RON and a 92.8 MON. Blending octanes were calculated for the experimental alkylate from blend octanes and the known octanes of the reference alkylate. NEAT octane(no reference alkylate solvent) was obtained on the light alkylate sample. There was inadequate amount of the heavy alkylate to permit a similar test.

The reference alkylate was prepared in a Phillips HF alkylation unit operating on a mixed butene olefin feed.

EXAMPLE 8

Liquid Phase Alkylation Using A Well-Stirred Reactor

A catalyst preparation step and experimental operating procedure similar to Example 4 were used except that the tubular reactor was replaced by a dual stage stirred reactor. The volume of the first stage was 40 cc and the volume of the second stage was 35 cc. Alkylation was conducted by feeding i-butane, catalyst and 2-butene to the first stage. Product from the first stage flowed into the second where additional 2-butene was added. Product from the second stage was collected and analyzed. Isobutane was fed at 180 cc/hr. Olefin feed rate to the first stage was 6 cc/hr. with the same rate being fed to the second stage. MIBAD and 1-chlorobutane activator were fed at rates sufficient to maintain 700 molar ppm of catalyst in the reactor with an activator to catalyst ratio of 1.4 mol/mol. The overall isobutane/olefin ratio was 15/1 mol/mol. The reactor was maintained at 180° F. and 650 psig and the stirrer was operated at 1,200 rpm. 100% olefin conversion was observed. The analysis of the product, from which the unreacted ibutane was removed is shown below. The Research Octane Number calculated by the method of Hutson and Logan (*Hydrocarbon Processing*, September, 1975) was 91. The Bromine Number was also determined. The value obtained, 1.8, showed the product to be virtually all paraffinic alkylate.

| Compounds | GC/MS Wt % |
|---|---|
| Isobutane | 4.1 |
| n-butane | 1.0 |
| Isopentane | 5.5 |
| n-Pentane | 2.9 |
| 2,3-Dimethylbutane | 2.7 |
| 2-Methylpentane | 1.3 |
| 3-Methylpentane | 0.5 |
| 2,4-Diemthylpentane | 3.0 |
| 2,2,3-Trimethylbutane | 0.3 |
| 2-Methylhexane | 1.0 |
| 2,3-Dimethylpentane | 2.0 |
| 3-Methylhexane | 0.6 |
| 2,2,4-Trimethylpentane | 21.0 |
| 2,2-Dimethylhexane | 0.1 |
| 2,4,4-Trimethyl-2-pentane | 0.2 |
| 2,5-Dimethylhexane | 4.8 |
| 2,4-Dimethylhexane | 5.0 |
| 2,2,3-Trimethylpentane | 3.3 |
| 2,3,4-Trimethylpentane | 4.6 |
| 2,3,3-Trimethylpentane | 5.3 |
| 2,3-Dimethylhexane | 2.0 |
| C8-ane | 1.1 |
| C8-ane | 1.0 |
| 2,2,5-Trimethylhexane | 3.1 |
| C9-ane | 0.5 |
| C9-ane | 0.4 |
| C8-ane | 0.4 |
| C10-ane | 0.3 |
| C10-ane | 0.5 |
| C10-ane | 0.5 |
| C10-ane | 0.6 |
| C11-ane | 0.5 |
| C11-ane | 0.2 |
| C12-ane | 0.2 |
| TOTAL | 81.7 |

Although the invention has been described with reference to its preferred embodiments, those of ordinary skill in the art may, upon reading this disclosure, appreciate changes and modifications which do not depart from the scope and spirit of the invention as described above or claimed hereafter.

I claim:

1. A method for alkylating a hydrocarbon having at least four carbon atoms or isomerizing a hydrocarbon having at least four carbon atoms to a different molecular structure, comprising the steps of:

forming a Lewis acid-hydrocarbon complex catalyst comprising the product of reaction of at least
  (a) a Lewis acid of the formula $R_{(m-2-z)}MX_{2+z}$ wherein M is a Group 3a, 5a or 5b metal, X is a halide, R is a hydrocarbyl radical having 1 to 12 carbon atoms, "m" is an integer equal to the greatest oxidation state of M, and "z" is an integer of 0, 1 or m−2;
  (b) a hydrogen halide; and
  (c) an organic compound selected from
    (1) first paraffins having 12 or fewer carbon atoms, or
    (2) olefins having 12 or fewer carbon atoms, or
    (3) ethers having 6 or fewer carbon atoms,
said product of reaction dissolved in a liquid second paraffin hydrocarbon to form a solution;
maintaining the solution containing the product of reaction dissolved in the liquid second paraffin hydrocarbon at a temperature such that the catalyst does not precipitate for a time sufficient for alkylation or isomerization to occur in said solution; adding the hydrocarbon to be alkylated or isomerized to yield isomerized or alkylated product hydrocarbon; and
separating the isomerized or alkylated product hydrocarbon compound from the Lewis acid-hydrocarbon complex catalyst.

2. The method of claim 1, further characterized by the Lewis acid-hydrocarbon complex catalyst comprising a transition metal halide selected from the group consisting of zirconium halides and cuprous halides.

3. The method of claim 2, wherein the Lewis acid-hydrocarbon complex catalyst has a molar ratio of M to a transition metal atom selected from the group consisting of zirconium and cuprous of from about 0.5 to about 1.0.

4. The method of claims 1 or 2 wherein the Lewis acid is of the formula $R_{m-2-z}$ $AlX_{2+z}$ and X is cloride or bromide and hydrogen halide is HCl or HBr.

5. The method of claim 4, wherein the Lewis acid is $R_{1-z}AlCl_{2+z}$ and the hydrogen halide is HCl.

6. The method of claim 4, wherein the Lewis acid is $AlCl_3$ or isobutylaluminum dichloride.

7. The method of claims 1 or 2, further characterized by maintaining said solution above its critical temperature and above its critical pressure.

8. The method of claim 7, wherein the Lewis acid is of the formula $R_{(m-2-z)}$ $AlX_{2+z}$ and X is chloride or bromide and the hydrogen halide is HCl or HBr.

9. The method of claim 8, wherein the Lewis acid is $R_{1-z}AlCl_{2+z}$ and the hydrogen halide is HCl.

10. The method of claim 7, further characterized by said solution containing a solvent selected from methane, ethane, propane, sulfur dioxide, nitrogen oxides, low molecular weight halocarbons, rare earth gases, and carbon dioxide.

11. The method of claim 10, further characterized by said solution containing a solvent selected from methane, ethane or propane.

12. The process of claim 10, wherein the hydrocarbon is a normal $C_{4-12}$ hydrocarbon and the product of isomerization is an iso $C_{4-12}$ hydrocarbon.

13. The process of claim 12, wherein the normal hydrocarbon is a normal paraffin and the product of isomerization is an iso paraffin.

14. The process of claim 12, wherein the normal hydrocarbon is n-butane and the product of isomerization is i-butane.

15. The process of claim 10, wherein the hydrocarbon to be alkylated is a mixture of a $C_{4-12}$ isoalkane and a $C_{3-5}$ olefin which is contacted with said solution thereby alkylating the olefin with the isoalkane to yield a product hydrocarbon comprising branched hydrocarbon compounds having a greater number of carbon atoms than either of the isoalkane or olefin.

16. The process of claim 15, wherein the isoalkane is i-butane and the olefin is 2-butene.

17. The process of claim 12 or 15, further characterized by separating the product hydrocarbon by increasing the temperature or decreasing the pressure of said solution thereby precipitating the metal halide Lewis acid-hydrocarbon complex catalyst out of solution.

18. The process of claim 1 or 2 wherein the hydrocarbon to be isomerized is a normal $C_{4-6}$ hydrocarbon having from 4 to 12 carbon atoms which is maintained at a temperature of from about 60° to about 130° C. and under a pressure sufficient to maintain said solution and the n-alkane in a liquid state and the product of isomerization is an isoalkane.

19. The method of claim 18, wherein the Lewis acid-hydrocarbon complex catalyst has a molar ratio of M to a transition metal atom selected from the group consisting of zirconium and cuprous of from about 0.5 to about 1.0.

20. The method of claim 18, wherein the Lewis acid is of the formula $R_{(m-2-z)} AlX_{2+z}$ and X is chloride or bromide and the hydrogen halide is HCl or HBr.

21. The method of claim 20, wherein the Lewis acid is $R_{1-z}AlCl_{2+z}$ and the hydrogen halide is HCl.

22. The method of claim 21, wherein the Lewis acid is $AlCl_3$ or isobutylaluminum dichloride.

23. The method of claim 20, wherein the hydrocarbon is a normal alkane and product of isomerization is an isoalkane.

24. The method of claim 23, wherein the normal hydrocarbon is a normal butane and the product of isomerization is isobutane.

25. The process of claim 1 or 2 further characterized by adding an isoalkane having from 4 to 12 carbon atoms to said solution and maintaining said solution and isoalkane at a temperature of from about 60° to about 105° C. and under a pressure sufficient to maintain said solution and isoalkane in a liquid state while contacting said solution and isoalkane with an olefin having from 3 to 5 carbon atoms, the product of the alkylation of the olefin with the isoalkane comprising branched hydrocarbon compounds having a greater number of carbon atoms than either of the isoalkane or olefin.

26. The process of claim 26, wherein the isoalkane is isobutane.

27. The process of claim 26, further characterized by maintaining said solution at a temperature of from about 82° to about 105° C.

28. The process of claim 27, wherein the olefin is a butene.

29. The process of claim 26, wherein the Lewis acid is of the formula $R_{(m-2-z)} AlX_{2+z}$ and X is chloride or bromide and the hydrogen halide is HCl or HBr.

30. The process of claim 29, wherein the Lewis acid is $R_{1-z}AlCl_{2+z}$ and the hydrogen halide is HCl.

31. The process of claim 30 wherein the Lewis acid is $AlCl_3$ or isobutylaluminum dichloride.

32. The process of claim 29, wherein the isoalkane is isobutane and the olefin is a butene.

33. The process of claim 32, wherein the butene is 2-butene.

34. The process of claim 32, further characterized by maintaining said solution a temperature of from about 88° to about 105° C.

35. The method of claim 1 further characterized by maintaining the concentration of catalyst from about 3.0 to about 22.5 millimoles per 1,000 grams of said solution and maintaining the molar ratios of hydrogen halide and the organic compound of the forming step relative to the Lewis acid from about 0.5 to about 1.5.

* * * * *

UNITED STATES PATENT AND TRADEMARK OFFICE
CERTIFICATE OF CORRECTION

PATENT NO. : 5,406,018
DATED : April 11, 1995
INVENTOR(S) : Larry G. Sherman

It is certified that error appears in the above-indentified patent and that said Letters Patent is hereby corrected as shown below:

Column 29, line 27, delete $--C_{4-6}--$.

Signed and Sealed this

Fifteenth Day of August, 1995

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,406,018
DATED : April 11, 1995
INVENTOR(S) : Larry G. Sherman

It is certified that error appears in the above-indentified patent and that said Letters Patent is hereby corrected as shown below:

Column 28, line 46, delete "$R_{m-2-z}AlX_{2+z}$" and insert --$R_{(m-2-z)}AlX_{2+z}$--

Signed and Sealed this

Seventh Day of October, 1997

*Attest:*

BRUCE LEHMAN

*Attesting Officer*      Commissioner of Patents and Trademarks